United States Patent
Ma et al.

(10) Patent No.: US 9,649,113 B2
(45) Date of Patent: May 16, 2017

(54) DEVICE FOR MONITORING PHYSIOLOGICAL PARAMETERS IN VIVO

(75) Inventors: Yong Ma, Cheshire, CT (US); Nelson Scarborough, Andover, MA (US); Marisha Godek, Fort Collins, CO (US); Rohan Shah, New Haven, CT (US); James Power, Madison, CT (US); Nilay Mukherjee, Lexington, MA (US); Frank Viola, Sandy Hook, CT (US); Edward McKenna, Boulder, CO (US); Shannon Campbell, Boulder, CO (US)

(73) Assignee: Covidien LP, Mansfield, MA (US)

( * ) Notice: Subject to any disclaimer, the term of this patent is extended or adjusted under 35 U.S.C. 154(b) by 845 days.

(21) Appl. No.: 13/438,012

(22) Filed: Apr. 3, 2012

(65) Prior Publication Data

US 2012/0273548 A1  Nov. 1, 2012

Related U.S. Application Data

(60) Provisional application No. 61/479,552, filed on Apr. 27, 2011.

(51) Int. Cl.
*A61B 17/04* (2006.01)
*A61B 17/11* (2006.01)
(Continued)

(52) U.S. Cl.
CPC .......... *A61B 17/1114* (2013.01); *A61B 5/076* (2013.01); *A61B 5/6847* (2013.01);
(Continued)

(58) Field of Classification Search
CPC .... A61B 2017/00367; A61B 17/07292; A61B 2017/00022; A61B 2017/00115;
(Continued)

(56) References Cited

U.S. PATENT DOCUMENTS 4,930,674 A * 6/1990 Barak ........................ 227/179.1
5,330,486 A 7/1994 Wilk
(Continued)

OTHER PUBLICATIONS

Australian Examination Report dated Apr. 16, 2013 in corresponding Australian Application No. 2012202180.

*Primary Examiner* — Robert Long

(57) ABSTRACT

A monitoring system is disclosed for in vivo monitoring of preselected physiological parameters associated with acute and/or chronic tissue compromise or failure in one or multiple tissue/organ sites in real time. In one method, a body portion of a surgical stapling device is positioned adjacent a first tissue section, an anvil assembly adapted to engage the body portion is positioned adjacent a second tissue section, and a monitoring device is positioned adjacent the first and/or second tissue sections. The monitoring device includes a sensor adapted to measure a preselected physiological parameter and a transmitter for transmitting signal to an extracorporeal receiving unit. The surgical stapling device is fired to mechanically secure the first and second tissue sections with at least one staple and the preselected physiological parameter is monitored via the information transmitted from the monitoring device to the receiving unit.

13 Claims, 3 Drawing Sheets

(51) Int. Cl.
*A61B 17/06* (2006.01)
*A61B 17/064* (2006.01)
*A61B 17/115* (2006.01)
*A61B 5/00* (2006.01)
*A61B 5/07* (2006.01)
A61B 17/072 (2006.01)
A61B 17/00 (2006.01)
A61B 5/053 (2006.01)
A61B 5/145 (2006.01)

(52) U.S. Cl.
CPC .... *A61B 17/0644* (2013.01); *A61B 17/06166* (2013.01); *A61B 17/1155* (2013.01); *A61B 5/0084* (2013.01); *A61B 5/0538* (2013.01); *A61B 5/14503* (2013.01); *A61B 5/6882* (2013.01); *A61B 17/07292* (2013.01); *A61B 2017/00022* (2013.01); *A61B 2017/00115* (2013.01); *A61B 2017/00119* (2013.01); *A61B 2017/00221* (2013.01); *A61B 2017/06176* (2013.01); *A61B 2017/1135* (2013.01)

(58) Field of Classification Search
CPC ........ A61B 2019/464; A61B 2019/465; A61B 2019/4836; A61B 2017/00017
USPC ...... 227/175.1–182.1; 606/75, 111, 138, 219
See application file for complete search history.

(56) References Cited

U.S. PATENT DOCUMENTS

| | | | |
|---|---|---|---|
| 5,383,880 A * | 1/1995 | Hooven | A61B 17/07207 227/175.1 |
| 5,389,098 A * | 2/1995 | Tsuruta | A61B 17/00234 606/142 |
| 5,395,033 A * | 3/1995 | Byrne et al. | 227/175.1 |
| 5,476,206 A * | 12/1995 | Green et al. | 227/176.1 |
| 5,518,163 A * | 5/1996 | Hooven | 227/5 |
| 5,669,918 A * | 9/1997 | Balazs et al. | 606/139 |
| 5,782,397 A * | 7/1998 | Koukline | A61B 17/0686 227/119 |
| 5,833,603 A | 11/1998 | Kovacs et al. | |
| 5,902,236 A * | 5/1999 | Iversen | A61B 5/0422 600/378 |
| 5,915,616 A | 6/1999 | Viola et al. | |
| 6,486,588 B2 | 11/2002 | Doron et al. | |
| 7,125,382 B2 | 10/2006 | Zhou et al. | |
| 7,297,112 B2 | 11/2007 | Zhou et al. | |
| 7,416,530 B2 | 8/2008 | Turner et al. | |
| 7,657,297 B2 | 2/2010 | Simpson et al. | |
| 7,686,762 B1 | 3/2010 | Najafi et al. | |
| 8,356,740 B1 * | 1/2013 | Knodel | A61B 17/07207 227/175.1 |
| 8,486,070 B2 * | 7/2013 | Morgan | A61B 5/0031 606/62 |
| 8,529,599 B2 * | 9/2013 | Holsten | A61B 17/0682 227/175.1 |
| 8,727,197 B2 * | 5/2014 | Hess | A61B 17/105 227/176.1 |
| 8,915,866 B2 * | 12/2014 | Nycz | A61B 5/076 600/586 |
| 2002/0095175 A1 * | 7/2002 | Brock et al. | 606/205 |
| 2002/0117534 A1 * | 8/2002 | Green et al. | 227/176.1 |
| 2004/0094597 A1 * | 5/2004 | Whitman et al. | 227/180.1 |
| 2004/0236192 A1 | 11/2004 | Necola Shehada et al. | |
| 2004/0243207 A1 * | 12/2004 | Olson | A61N 1/05 607/116 |
| 2005/0004478 A1 | 1/2005 | Fitz | |
| 2005/0131390 A1 * | 6/2005 | Heinrich et al. | 606/1 |
| 2005/0158360 A1 * | 7/2005 | Falotico et al. | 424/424 |
| 2005/0165317 A1 | 7/2005 | Turner et al. | |
| 2005/0173490 A1 * | 8/2005 | Shelton | 227/175.2 |
| 2006/0089547 A1 * | 4/2006 | Sarussi | A61B 5/0059 600/310 |
| 2006/0200012 A1 | 9/2006 | Mansour et al. | |
| 2006/0200220 A1 | 9/2006 | Brown et al. | |
| 2006/0212069 A1 * | 9/2006 | Shelton | 606/205 |
| 2007/0027371 A1 | 2/2007 | Benaron et al. | |
| 2007/0084896 A1 * | 4/2007 | Doll et al. | 227/175.2 |
| 2008/0033273 A1 | 2/2008 | Zhou et al. | |
| 2008/0058652 A1 | 3/2008 | Payne | |
| 2008/0108885 A1 | 5/2008 | Colvin, Jr. | |
| 2008/0149685 A1 * | 6/2008 | Smith et al. | 227/181.1 |
| 2008/0154101 A1 | 6/2008 | Jain et al. | |
| 2008/0154288 A1 | 6/2008 | Belson | |
| 2008/0287788 A1 | 11/2008 | Richardson et al. | |
| 2009/0001128 A1 * | 1/2009 | Weisenburgh, II | A61B 17/064 227/179.1 |
| 2009/0054908 A1 | 2/2009 | Zand et al. | |
| 2009/0114701 A1 * | 5/2009 | Zemlok et al. | 227/176.1 |
| 2009/0130021 A1 | 5/2009 | Munch et al. | 424/9.1 |
| 2009/0134200 A1 * | 5/2009 | Tarinelli et al. | 227/180.1 |
| 2009/0163782 A1 | 6/2009 | Shehada et al. | |
| 2009/0212088 A1 | 8/2009 | Okada et al. | |
| 2009/0234248 A1 | 9/2009 | Zand et al. | |
| 2009/0299153 A1 | 12/2009 | Gerber et al. | |
| 2010/0081895 A1 | 4/2010 | Zand | |
| 2010/0106194 A1 * | 4/2010 | Bonutti | A61B 17/0218 606/279 |
| 2011/0017801 A1 * | 1/2011 | Zemlok et al. | 227/175.1 |
| 2012/0193396 A1 * | 8/2012 | Zemlok et al. | 227/177.1 |
| 2012/0273548 A1 * | 11/2012 | Ma | A61B 17/06166 227/176.1 |
| 2013/0172717 A1 * | 7/2013 | Halpern | A61B 5/0478 600/378 |

* cited by examiner

DEVICE FOR MONITORING PHYSIOLOGICAL PARAMETERS IN VIVO

CROSS REFERENCE TO RELATED APPLICATION

The present application claims the benefit of and priority to U.S. Provisional Application Ser. No. 61/479,552, filed on Apr. 27, 2011, the entire contents of which are incorporated herein by reference.

TECHNICAL FIELD

The present disclosure relates to a system for real time monitoring of a patient's health and, more particularly, to real time monitoring devices for sensing physiological parameters of interest in vivo for early detection of medical needs of a patient over a pre-determined period of time.

BACKGROUND

Following surgery on the gastrointestinal system in which the bowel undergoes anastomosis, there is an incidence of subsequent leakage from the bowel into the peritoneal cavity which occurs in about 1-8% of patients. The results of this complication are a high morbidity and mortality rate that dramatically affects the patient's prognosis and largely impacts the cost of treatment. Leak detection is generally accomplished by monitoring clinical signs of infection, including white blood cell count, fever, malaise, heart rate, etc. A recognized problem of using clinical signs is that there is a lag between the time the leak occurs and the onset of signs or symptoms. This results in the severity of the problem escalating prior to its detection and the appropriate treatment being instituted.

Imaging modalities, such as fluoroscopy, may be utilized to monitor for leak detection after administering radiopaque dye orally or rectally. Imaging modalities, however, also have limitations of sensitivity and specificity, and require significant resources and cost to perform. Additional leak detection attempts of measuring effluent from drains have demonstrated some success. Limitations of this approach, however, include the inconsistent use of drains due to concomitant complications (e.g., infection, clogging, migration, etc.) and identification of markers from drain fluid may be delayed significantly after the leak occurs.

While devices are available in attempts to identify leaks, it would be advantageous to provide a real time monitoring system for effective early detection of issues associated with a patient's health. Such a device would provide a clinician with a method of evaluating critical predictors of morbidity and mortality in patients in real time following surgery and/or tissue trauma. Acute stage detection would allow for early intervention resulting in improved patient outcomes.

SUMMARY

In accordance with the present disclosure, a monitoring system for in vivo monitoring of preselected physiological parameters associated with acute and/or chronic tissue compromise or failure in one or multiple tissue/organ sites in real time is disclosed. In one method of real time monitoring of an anastomosis, a body portion of a surgical stapling device including a staple cartridge is positioned adjacent a first tissue section, an anvil assembly including a shaft adapted to engage the body portion is positioned adjacent a second tissue section, and a monitoring device is positioned adjacent the first and/or second tissue sections. The monitoring device includes a sensor adapted to measure a preselected physiological parameter and a transmitter for transmitting signal to an extracorporeal receiving unit. The surgical stapling device is fired to mechanically secure the first and second tissue sections with at least one staple along a staple line and the preselected physiological parameter is monitored via the information transmitted from the monitoring device to the receiving unit. The extracorporeal receiving unit may be connected to the sensor and or monitoring device wirelessly or by wires. In the instance of a wired connection, the wires and/or monitor and sensor may be attached to a drain or other transcorporeal device. Such placement allows easy removal of the monitor and transmission system.

An example of an example of a physiological parameter is the presence of an analyte indicative of an anastomatic leakage. The analyte to be detected can be an endogenous material that would normally only be present within the body system (intestines, etc.) such as $E.$ $coli$ or blood, or an exogenous material introduced into the body system that would remain within the system unless a leakage occurs. The advantage of external analytes is that they may allow higher sensitivity for detection as the normal physiological amount is zero. External analytes may be administered orally or by other means of introduction into the digestive tract or may be administered intravenously. Analytes may be administered in combination, For example, an analyte may enhance detection of normally present endogenous material and a second analyte may be an external analyte.

An alternative embodiment uses a drain or other collection device that allows for the analyte to be collected and then measured extracorporeally, such as with an in vitro diagnostic (IVD) kit.

In embodiments where the fluid is collected extracorporeally, the fluid can be analyzed by collecting fluid, placing it into a device that does the analysis, then running an assay, or can be collected into an integrated system that would automatically perform the analysis and generate a signal to the monitoring site. Examples of these are glucose monitoring which can be performed by collecting blood and then testing vs. an integral monitor that automatically performs the analysis and provides feedback.

The body systems envisioned include gastrointestinal, vascular, pulmonary, urinary, bile, or any other systems wherein fluids are contained within organs or lumens.

The step of positioning a monitoring device may include placing the monitoring device on a portion of the first and/or second tissue section external of the staple line. In some embodiments, the monitoring device may be affixed to the tissue with a biocompatible adhesive. In other embodiments, the monitoring device may be affixed to the tissue with a surgical fastener.

The step of positioning a monitoring device may include positioning a surgical implant including the monitoring device about the tissue sections. In embodiments, a buttress including the monitoring device may be placed on the shaft of the anvil assembly. In some embodiments, an anastomosis ring including the monitoring device and having first and second separable members may be placed onto the body portion and shaft of the surgical stapling device. In other embodiments the monitoring device may be positioned in the immediate region of a staple line by using a bioadhesive, a suture, a staple or a clip, either attaching the monitor to tissue, or to a feature of the staple line, such as a buttress or a portion of a staple.

The method may further include providing staples including at least one monitoring device affixed thereto within the staple cartridge of the surgical stapling device. The staples may have at least one monitoring device on a crown of the staple and at least one monitoring device on a leg of the staple such that upon firing the surgical stapling device the first and second tissue sections are positioned between the monitoring devices of the staple.

The step of monitoring the preselected physiological parameter may include waiting for an alert from the receiving unit. The receiving unit may be worn on a body of a patient.

In embodiments, the step of monitoring the preselected physiological parameter may include introducing an exogenous marker into the first and second tissue sections.

In accordance with another embodiment of monitoring tissue in real time, a surgical fastener including a monitoring device containing a sensor adapted to measure a preselected physiological parameter and a transmitter for transmitting signal from the sensor may be positioned about tissue in a body of a patient. An extracorporeal receiving unit for collecting data from the monitoring device is positioned in proximity to the body of the patient. The receiving unit includes an indicator to alert the patient and medical staff when a predetermined test criterion of the preselected physiological parameter is met. The extracorporeal receiving unit may be placed on the body of patient.

BRIEF DESCRIPTION OF THE DRAWINGS

Various embodiments of the present disclosure will be described herein with references to the accompanying drawings, wherein.

DETAILED DESCRIPTION OF THE EMBODIMENTS

Various exemplary embodiments of the present disclosure are discussed hereinbelow in terms of systems for measuring physiological parameters associated with acute and/or chronic tissue compromise or failure in one or multiple tissue/organ sites in real time. While the present disclosure is directed to the detection of leaks of gastrointestinal content into the abdomen following anastomosis, it is envisioned that the principles of the present disclosure are equally applicable to a range of in vivo diagnostic applications related to monitoring of surgical and medical treatments of disease and body ailments of a patient, such as necrosis, infection, and cancer. For example, devices of the present disclosure may be utilized in the detection of infection, metabolic disorder, or other abnormal or non-ideal conditions of wound healing.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

The following discussion includes a description of embodiments of the presently disclosed system for real time monitoring and analysis of physiological parameters, as well as a description of exemplary corresponding methods of use in accordance with the principles of the present disclosure.

Figure 1:
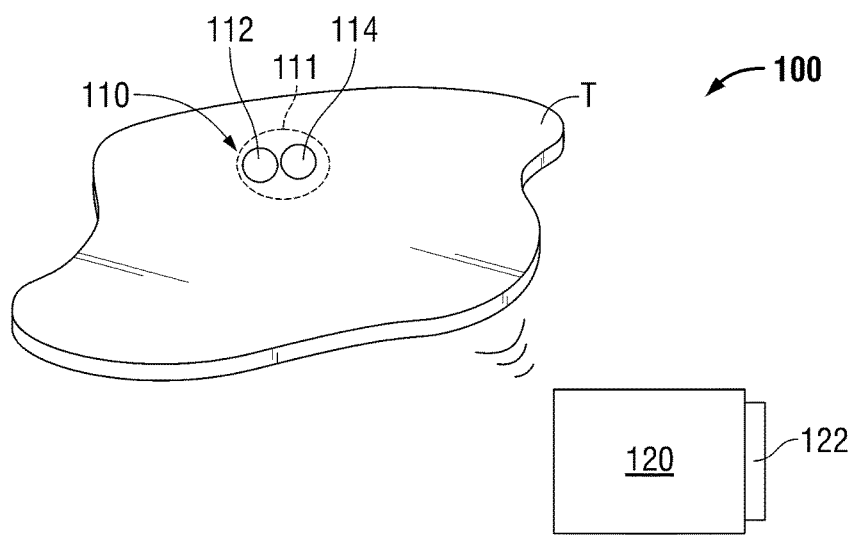
FIG. 1 is a schematic illustration of a real time tissue monitoring system in accordance with one embodiment of the present disclosure.

Referring now to the figures, wherein like components are designated by like reference numerals throughout the several views, FIG. 1 illustrates a tissue monitoring system 100 for use in real time monitoring and diagnoses of physiological parameters of interest that are related to patient health in accordance with one embodiment of the present disclosure. The system 100 includes a monitoring device 110 including a sensor 112 and a transmitter 114, and a receiving unit 120. The sensor 112 measures a physiological parameter of interest in vivo and the transmitter 114 converts the measurement from sensor 112 into signal which may be transmitted to receiving unit 120 to collect the measurement data in real time. The signals produced contain information about a specific characteristic of the tissue or tissue environment, which in turn imparts information about the condition or state of the tissue which can be utilized in determining a proper course of treatment dependent upon the information received. In embodiments, the monitoring device 110 is wireless and/or does not include a battery. In such embodiments, the monitoring device may be powered externally, such as by receiving unit 120 via RF or magnetic telemetry, to run continuously or be activated intermittently to collect data as needed. Such embodiments eliminate issues associated with battery leakage, encapsulation and retraction of embedded wires, among other issues within the purview of those skilled in the art.

Receiving unit 120 is configured as an extracorporeal device for collecting data from monitoring device 110. The data collected may provide a sensory alert via an indicator 122 to the patient and/or clinician when a predetermined test criterion is met to allow for appropriate medical response based on the information received. Indicator 122 may be a visual indicator such as a light that illuminates or changes color upon detection of a pre-selected parameter, an audio indicator such as a speaker, or other sensory indicator within the purview of those skilled in the art. In embodiments, receiving unit 120 may be worn by the patient, such as in a wristwatch, or may be housed within a carrying bag or pouch. In such embodiments, the monitoring system allows for patient mobility and post-surgical monitoring at home.

The sensor 112 may be a conductivity/resistivity sensor for measuring ionic concentration of a compound; an optical sensor such as a CCD or CMOS image sensor; an electrical, electrochemical, or chemical sensor for measuring characteristics such as impedance, temperature, pH, enzymatic activity, etc; a mechanical sensor; a biochemical sensor for measuring the presence and/or levels of analytes; an acoustic sensor such as an ultrasound; a light sensor such as a photodiode; or other sensor within the purview of those skilled in the art for measuring and/or identifying a physiological condition or state, such as tissue perfusion, tissue ischemia and/or reperfusion, pH, bacterial load, temperature, pressure, protein or bioactivity factors, metabolic analytes, and other biomarkers or parameters of interest.

Sensor 112 and transmitter 114 may be fabricated from any biocompatible material that has suitable physical properties for the intended use in vivo, or may be disposed within a housing 111 (shown in phantom) fabricated from a biocompatible material. The biocompatible material should be non-fouling, non-damaging to surrounding tissues, and resistant to device-related infection. In embodiments, the sensor 112, transmitter 114, and/or housing 111 should be fabricated from a material which will not trigger a fibrotic response over the term of use. Alternatively, a fibrotic response may be utilized to encapsulate the monitoring device 110 after the device's useful lifetime has ended. Thus, the monitoring device 110 may be placed, i.e., made indwelling, in a temporary or permanent fashion adjacent a tissue of interest in a location which allows for the sensor 112 to detect the physiological parameter of interest, e.g., for the intestine, either on the serosal or intraluminal surface.

Figure 2A:
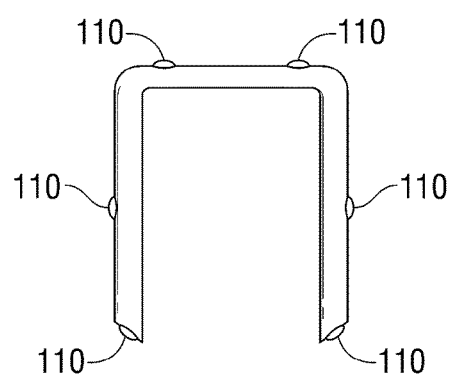
FIGS. 2A-2F are perspective views of surgical devices which may include a monitoring device in accordance with the principles of the present disclosure.
Figure 2B:
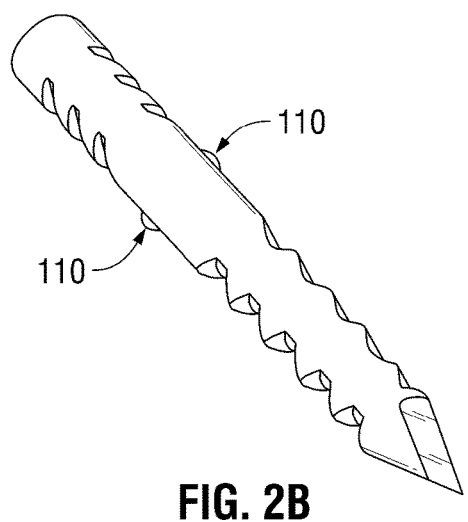
Figure 2D:
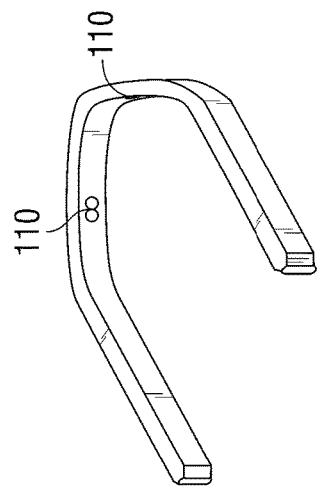
Figure 2F:
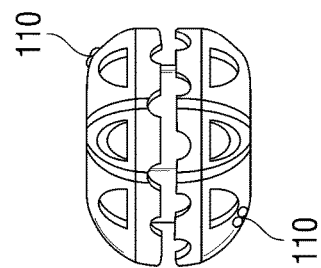
Figure 2C:
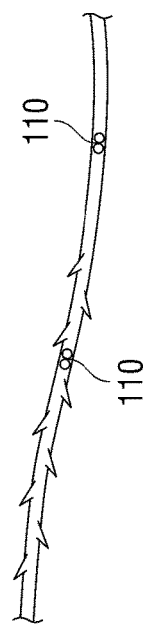
Figure 2E:
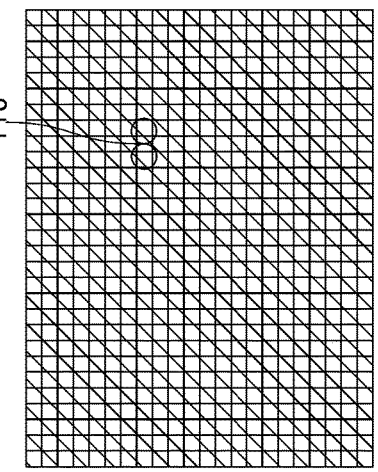

Monitoring device 110 is adapted for placement within the body at a specific anatomical site. Monitoring device 110 may be placed within a body cavity, at a tissue surface, or in contact with bodily fluids, such as blood, to monitor the pre-selected physiological parameter(s). As illustrated in the present embodiment, the monitoring device 110 is embedded within tissue "T". Monitoring device 110 may be attached to tissue "T" with a biocompatible adhesive or a surgical fastener such as a suture or staple. In embodiments, monitoring device 110 may be placed in a location using resorbable fasteners so that the monitoring device 110 may be expelled from the body once the fasteners is absorbed or broken down by the body, and the monitoring device 110 is no longer needed for monitoring. For example, the monitoring device may be placed within the rectum, allowing for easy passage out of the patient's body. Other sites within the alimentary canal are envisioned, as well as the pulmonary and urinary tract. Alternatively, monitoring device 110 may be attached to a degradable and/or non-degradable medical or surgical implant, such as a staple (FIG. 2A), tack (FIG. 2B), suture (FIG. 2C), clip (FIG. 2D), mesh (FIG. 2E), anastomosis ring (FIG. 2F), etc.

The monitoring device 110 may be maintained in vivo for a pre-determined period of time coinciding with the sensing time required of the device, functioning continuously or intermittently over the period of time. In embodiments of intermittent use, the monitoring device 110 may take measurements at pre-determined intervals such that the monitoring device 110 is idle, i.e., does not take measurements, to conserve power at most times. The reporting periodicity of the monitoring device 110 may be altered to accommodate the test parameter of interest. For example, the monitoring device 110 may report at one minute increments for the first ten to sixty minutes following implantation, then once an hour for the next two or three days. In embodiments, the monitoring device 110 is utilized over a period of time relevant to critical acute conditions which may be life threatening. In embodiments, the monitoring device 110 may be utilized for an hour to about a week or more, as required. The frequency of tissue monitoring and data collection may be controlled by receiving unit 120, in embodiments, a clinician may control the time and frequency of data collection by adjusting the measurement parameters via controls on receiving unit 120.

The monitoring device 110 may be a single use, or multiple use, device. In embodiments in which the monitoring device 110 is for single use, use of the monitoring device 110 ceases after the sensor has reached a predetermined number of readings or after the presence and/or level of a pre-selected parameter has been reached. In embodiments in which the monitoring device 110 is for multiple use, the monitoring device 110 may be maintained in vivo for a pre-determined period of time and function over short periods of time relevant to critical acute conditions which may be potentially life threatening.

In embodiments, two or more monitoring devices 110 or sensors 112, e.g., an array of sensors 112, may be used concomitantly to provide a comprehensive view of tissue health located adjacent to, or distant from, the tissue site, as described in more detail below. The data collected from the monitoring devices 110 may be used to evaluate tissue health and may have predictive value for the occurrence of serious or life threatening condition, e.g., post-surgical infection, anastomotic leaks, etc. In embodiments, the sensors 112 may measure the same physiological parameter in replicates, such as duplicate or triplicate, to improve the accuracy of testing. In other embodiments, the sensors may detect multiple parameters of interest to provide greater information about the patient's physiological state. For example, multiple analytes or parameters such as pH and temperature, and compression and oxygenation, may be measured simultaneously. Use of multiple sensors may improve the efficiency of testing and may save time and treatment costs.

Monitoring device 110 is placed within a patient's body in a location conducive to detecting the physiological parameter(s) of interest. In some embodiments, this may require intimate association with the tissue site of interest, while in other embodiments, tissue association may be less critical. For example, in a Roux-en-Y anastomosis procedure there are two or more sites of potential leakage from the gastrointestinal tract. Positioning of the monitoring device 110 will depend on the selectivity and sensitivity of the physiological parameter being analyzed, such as the diffusion of a biomarker through tissue or a body cavity.

Methods of utilizing the real time monitoring system of the present disclosure are also described. In one embodiment, the method may include accessing a surgical site, placing at least one monitoring device at the surgical site, and monitoring pre-selected physiological parameters of the surgical site via the information transmitted from the monitoring device to a receiving unit.

Figure 3A:
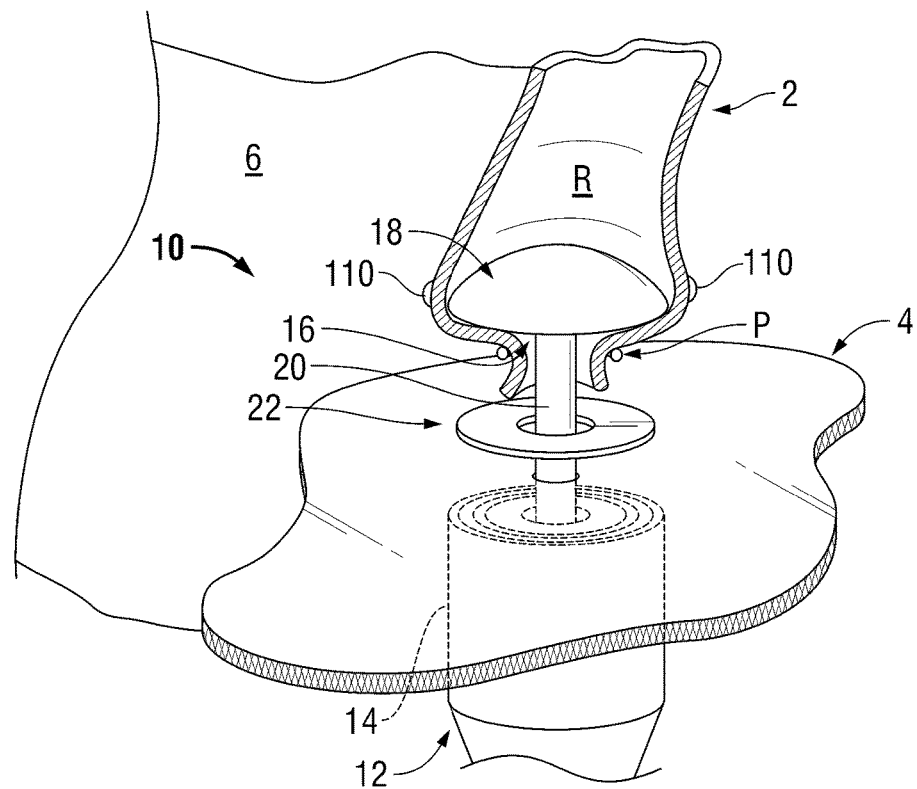
FIG. 3A is a perspective view in partial cross-section of monitoring devices of the present disclosure being utilized with a surgical stapling apparatus during an anastomsis procedure in accordance with the principles of the present disclosure.
Figure 3B:
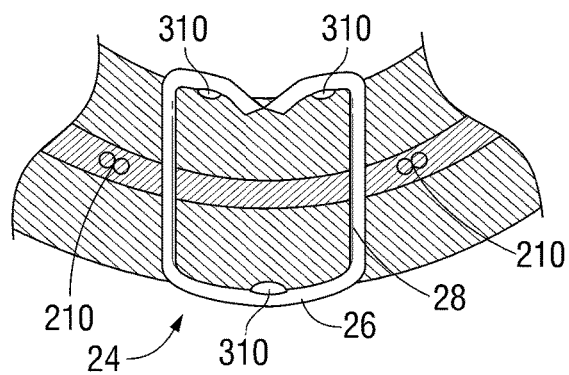
FIG. 3B is a cross-sectional view of tissue after completion of the anastomosis procedure of FIG. 3A.

As illustrated in FIGS. 3A and 3B, multiple monitoring devices 110, 210, 310 are placed intraoperatively at a surgical site during an anastomosis procedure. A surgical stapling device 10 is provided to effect the joining of intestinal sections 2 and 4. Surgical stapling device 10 includes a tubular body portion 12 terminating in a staple cartridge assembly 14. Positioned distally of staple cartridge 14 is an anvil assembly 16 including an anvil member 18 and a shaft 20 operatively associated therewith for removably connecting the anvil assembly 16 to a distal end portion of surgical stapling device 10. Surgical stapling devices are well known and include, for example, U.S. Pat. No. 5,915,616 to Viola et al., the contents of which are incorporated herein by reference in their entirety.

The anastomosis procedure is typically performed using minimally invasive surgical techniques including laparoscopic methods and instrumentation. At the point in the procedure shown in FIG. 3A, a diseased intestinal section has been previously removed, anvil assembly 16 has been applied to the operative site either through a surgical incision or transanally and positioned within intestinal section 2, tubular body portion 12 of surgical stapling device 10 has been inserted transanally into intestinal section 4, and one or more monitoring devices 110 have been positioned on an outer surface of intestinal section 2 within abdominal cavity 6 through the surgical incision or transanally as described above to detect leakage at the anastomosis site. Intestinal sections 2 and 4 are also shown temporarily secured about their respective components (e.g., shaft 20 of anvil assembly 16, and the distal end of tubular body portion 12) by conventional means such as a purse string suture "P".

Additionally, buttress 22, including monitoring device 210, may be placed on shaft 20 of anvil assembly 16 prior to the coupling of anvil assembly 16 to the distal end of tubular body portion 12. Following positioning of buttress 22 onto shaft 20 of anvil assembly 16, the clinician maneuvers anvil assembly 16 until the proximal end of shaft 20 is inserted into the distal end of tubular body portion 12 of surgical stapling device 10, wherein the mounting structure (not shown) within the distal end of tubular body portion 12 engages shaft 20 to effect the mounting.

Thereafter, anvil assembly 16 and tubular body portion 12 are approximated to approximate intestinal sections 2 and 4, and capture buttress 22 therebetween. Surgical stapling device 10 is then fired thereby stapling intestinal sections 2, 4 to one another and cutting the portion of tissue and buttress 22 disposed radially inward of a knife (not shown), to complete the anastomosis as illustrated in FIG. 3B.

Additionally, staples 24 include monitoring devices 310 about crown 26 and legs 28 thereby allowing a clinician to measure properties on each side of, and through, the stapled tissue. Thereafter, if one or more of the monitoring devices 110, 210, 310 transmits information that meets a specified test criterion, a course of treatment may be selected, such as, for example, antibiotic therapy, surgical intervention, etc. On the other hand, if no indicator of abnormal physiological condition or state is provided, no further action is required on the part of the clinician.

It is envisioned that other surgical fasteners may be utilized to secure the monitoring device within the tissue. For example, an anastomosis ring (FIG. 2F) including monitoring device 110 may be utilized. The anastomosis ring includes first and second separable unitary members which are configured to interlock together. One unitary member is positioned on the anvil assembly associated with a first tissue section and the other unitary member is positioned on the body portion of the surgical stapling device associated with the second tissue section. The first and second tissue sections are tightened around its respective unitary member and the surgical stapling device is actuated to close the unitary members to form the interlocked anastomosis ring and to clamp the first and second tissue sections together.

In other methods, an exogenous marker may be introduced into a patient as a means to detect the presence or absence of clinical conditions. In embodiments, a radiopaque dye may be fed through the tract "R" defined by the anastomosis shown in FIG. 3A above, to detect the presence of a leak. In the event that the radiopaque material enters the abdominal cavity 6 in which monitoring device 110 is placed, the sensor 112 of monitoring device 110 will measure the dye and the transmitter 114 will send a signal to receiving unit 120 (FIG. 1) to alert the patient and/or clinician. Various exogenous materials may be selected such that the properties of the material may be detected by sensor 112 by other methods, such as chemical properties.

In other embodiments, precursors may be introduced into the surgical site that would only be converted into detectable forms under certain circumstances. For example, a substrate including a compound specific to an analyte of interest, e.g., bacterial enzymes, may be positioned near sensor 112 of monitoring device 110, or a membrane may be disposed on a portion of monitoring device 110 that is selectively permeable to a particular analyte. In the event that bacteria enter abdominal cavity 6, the enzymes will convert the substrate or permeate into the membrane, resulting in a sensor 112 response that will be transmitted to receiving unit 120.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the system based on the above-described embodiments. Accordingly, the present disclosure is not to be limited by what has been particularly shown and described, except as indicated by the appended claims.

What is claimed is:

1. A method of real time monitoring of an anastomosis, the method comprising:
   positioning a body portion of a surgical stapling device including a staple cartridge adjacent a first tissue section;
   positioning an anvil assembly including a shaft adapted to engage the body portion of the surgical stapling device adjacent a second tissue section;
   implanting at least one staple including a plurality of monitoring devices adjacent the first tissue section or the second tissue section, each monitoring device of the plurality of monitoring devices comprising a sensor adapted to measure a preselected physiological parameter and a transmitter for transmitting signal to an extracorporeal receiving unit;
   firing the surgical stapling device to mechanically secure the first and second tissue sections with the at least one staple from the staple cartridge along a staple line; and
   monitoring the preselected physiological parameter via information transmitted from one of the monitoring devices of the plurality of monitoring devices to the extracorporeal receiving unit following completion of the anastomosis.

2. The method of claim 1, further comprising placing a buttress incorporating a monitoring device on the shaft of the anvil assembly.

3. The method of claim 2, further comprising affixing the buttress between the first and second tissue sections using the at least one staple from the staple cartridge of the surgical stapling device.

4. The method of claim 3, wherein firing the surgical stapling device includes the at least one staple having a first monitoring device of the plurality of monitoring devices on a crown of the at least one staple and a second monitoring device of the plurality of monitoring devices on a leg of the at least one staple.

5. The method of claim 4 wherein firing the surgical stapling device further includes positioning the first tissue section and the second tissue section between the first and second monitoring devices of the plurality of monitoring devices of the at least one staple.

6. The method of claim 1, wherein monitoring the preselected physiological parameter further includes sending a signal indicating a measurement of the preselected physiological parameter to the extracorporeal receiving unit.

7. The method of claim 1, further comprising wearing the extracorporeal receiving unit on a body of a patient.

8. The method of claim 1, wherein monitoring the preselected physiological parameter further includes introducing an exogenous marker into the first tissue section or the second tissue section.

9. A method of monitoring tissue in real time, the method comprising:

affixing a staple to tissue in a body of a patient during a surgical procedure, the staple including at least one monitoring device on a crown of the staple and at least one monitoring device on a leg of the staple, each monitoring device comprising a sensor adapted to measure a preselected physiological parameter and a transmitter for transmitting signal from the sensor; and positioning an extracorporeal receiving unit for collecting data from the monitoring device in proximity to the body of the patient following the surgical procedure, the extracorporeal receiving unit including an indicator to alert the patient when a predetermined test criterion of the preselected physiological parameter is met during post-surgical monitoring.

10. The method of claim 9, wherein positioning the extracorporeal receiving unit further includes placing the extracorporeal receiving unit on the body of the patient.

11. The method of claim 9, wherein affixing the staple further includes positioning tissue between the monitoring devices of the staple.

12. The method of claim 11, further comprising measuring properties on each side of, and through, the tissue via information transmitted from the monitoring devices of the staple.

13. The method of claim 4, wherein monitoring the preselected physiological parameter further includes measuring properties on each side of, and through, the first and second tissue sections.

* * * * *